United States Patent [19]
Mishima et al.

[11] Patent Number: 6,106,867
[45] Date of Patent: Aug. 22, 2000

[54] GELATINIZED PROPOLIS FOOD PRODUCTS

[75] Inventors: Satoshi Mishima, Gifu; Miho Tanaka, Gifu-ken, both of Japan

[73] Assignee: API Co., Ltd., Gifu-ken, Japan

[21] Appl. No.: 09/301,187

[22] Filed: Apr. 28, 1999

[30] Foreign Application Priority Data

Aug. 31, 1998 [JP] Japan .................................. 10-245211

[51] Int. Cl.⁷ .......................... A01N 63/00; A01N 65/00; A61K 35/64; C12N 5/02; C12N 5/06
[52] U.S. Cl. ........................ 424/539; 424/93.1; 424/93.7; 435/325; 435/348; 426/425; 426/443; 426/573; 426/655
[58] Field of Search .................................. 424/93.1, 93.7, 424/539; 435/325, 348; 426/573, 655, 425, 443

[56] References Cited

U.S. PATENT DOCUMENTS 4,382,886  5/1983  Sosnowski ............................... 260/107

FOREIGN PATENT DOCUMENTS 63-307825  12/1988  Japan .
2-167038   6/1990   Japan .
5-252883   10/1993  Japan .
8-252069   10/1996  Japan .

*Primary Examiner*—David M. Naff
*Assistant Examiner*—Deborah K. Ware
*Attorney, Agent, or Firm*—Crompton, Seager & Tufte, LLC

[57] ABSTRACT

A propolis food product that contains propolis active ingredients with improved bio-absorbability and is readily ingested. The propolis food products containing propolis extracts are gelled by gelatinizers. The gelantinizers are materials such as shiitake extracts, curdlan, agarics extracts and further including sulfated saccharides, β-glucans, carrageenan, locust bean gum, xanthan gum, or agar. The propolis food products are prepared by water or alcohol extraction. Furthermore, the steps involve preparing a gelantinizer solution by adding a gelatinizer to water and adding propolis extracts thereto so that the amount of the propolis extracts in the food product is from 2 to 25 w/w %, a gel composition is then formed by admixing the solution in order to uniformly disperse the propolis extracts.

13 Claims, 1 Drawing Sheet

GELATINIZED PROPOLIS FOOD PRODUCTS

BACKGROUND OF THE INVENTION

The present invention relates to food products containing propolis.

Propolis is a naturally occurring substance, which has long been used as a folk medicine, and is produced by honeybees. Propolis contains resin-like materials collected from various plants and glandular secretions of bees. Containing resins, beewax, essential oils, pollens, and flavonoids, propolis has been found to exhibit a variety of pharmacological effects on the human body. Among such effects are anti-microbial effects, anti-viral effects, anti-oxidative effects, anti-inflammetory effects, antitumor effects, local anasthetic effects, analgestic effects, and immuno-stimulating effects.

Of these effects, anti-oxidative effects, anti-inflammetory effects, analgestic effects, anti-viral effects, immuno-stimulating effects, antitumor effects are attributable to flavonoids present in propolis.

Propolis extracts containing flavonoids as active ingredients show high fluidity. Such extracts can be obtained by extracting crude propolis with alcohol or water. Alcohol extraction is preferred in that flavonoids are efficiently extracted and contamination with microorganisms is minimized.

One drawback of such propolis products is that the high fluidity of the product considerably shortens the time that propolis remains in human gastrointestinal (GI) tracts, leading to less absorption of propolis active ingredients through the GI tracts. Another problem with the alcohol-extracted propolis products is that they have a strong odor and are particularly irritating to mucous membranes due to their acrid, pungent taste characteristics. Therefore, such products are difficult to ingest.

SUMMARY OF THE INVENTION

The present invention addresses the above-mentioned problems associated with the prior art food products. Accordingly, it is an objective of the present invention to provide propolis food products having bio-absorbability of their active ingredients improved, and having reduced smells, which are less irritating to mucous membrane and, therefore, are easy to ingest without a help of water.

To achieve above objective, the present invention provides a propolis food product that has a gel form and contains propolis extracts.

Basically, the present invention provides a method for producing such a propolis food product that includes preparing a gelatinizer solution by adding at least one gelatinizer to water so that the amount of the gelatinizer in the food product is from 0.01 to 10 w/w %; adding propolis extracts to the gelatinizer solution so that the amount of the propolis extracts in the food product is from 2 to 25 w/w %; and forming a gel composition by admixing the solution to disperse the propolis extracts uniformly throughout the solution.

Other aspects and advantages of the present invention will become apparent from the following description, taken in conjunction with the accompanying drawings, illustrating by way of example the principles of the invention.

BRIEF DESCRIPTION OF THE DRAWINGS

The features of the present invention that are believed to be novel are set forth with particularity in the appended claims. The invention, together with objectives and advantages thereof, may best be understood by reference to the following description of the presently preferred embodiments together with the accompanying drawings in which:

DETAILED DESCRIPTION OF THE PREFERRED EMBODIMENTS

Figure 1:
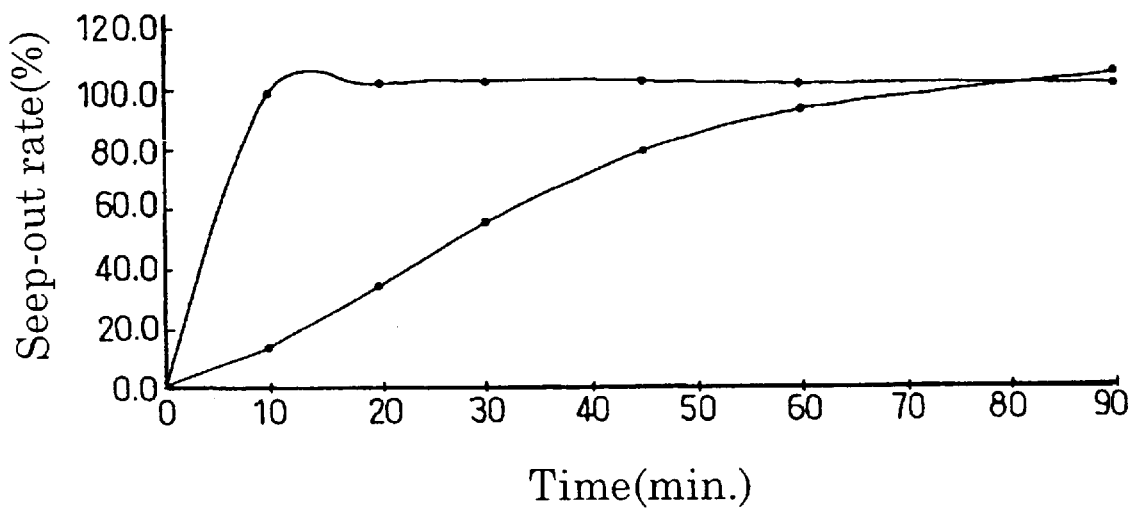
FIG. 1 is a graph showing a relationship between seep-out rate of flavonoids and time.

Preferred embodiments of the present invention will now be described in detail hereinafter.

The propolis food product of the present invention generally has a gel-like form and contains propolis extracts. The gel form of the product is typically formed using a gelatinizer such as polysaccharides. Alternatively, the product may be formed into a gel through the process of heating, without using a gelatinizer.

Crude propolis, a primary component of the propolis food products, is utilized in many different nations around the world, including Brazil, China, Japan, European countries, and Oceania countries. Crude propolis, which contains various physiologically active substances as well as other non-useful components, may be used without any processing. Alternatively, extracts of the crude product extracted by known methods may be used. Propolis as used hereinafter refers to either the crude products or the extracts thereof.

Commonly used extracts of crude propolis include components soluble to hydrophilic organic solvents (hereinafter referred to as alcohol-extracted propolis), and components that are water-soluble (hereinafter referred to as water-extracted propolis).

Propolis extracts are either alcohol-extracted or water-extracted after milling the crude propolis. Of these two methods, alcohol-extraction is preferred as it enables efficient extraction of flavonoids and prevents the extracts from being contaminated by microorganisms.

Flavonoids are a group of active ingredients found in propolis extracts. The term flavonoid is a general term for various plant pigments including flavones, flavanones, isoflavones, antocyans, and cathechin. A flavonoid is generated when one molecule of phenyl propane reacts with three molecules of acetic acid.

Preferably, polysaccharides and derivatives thereof may be used as a gelatinizer to gelatinize the propolis food products. In a gelatinizer, at least one polysaccharide or derivative thereof selected from the group consisting of pectin, agar, gum arabic, xanthan gum, gum tragacanth, karaya gum, gatthi gum, guar gum, locust bean gum, arginic acid, arginates (e.g., sodium arginate), carrageenan, gelatin, dextran, starches (e.g., corn, rice, wheat, potato, kudzu, tapioca, carboxymethyl starches), cellulose (e.g., hydroxypropylmethyl cellulose, carboxymethyl cellulose, methyl cellulose, methylethyl cellulose, crystallized cellulose), poly (vinyl alcohol), poly(vinylpyrrolidone), polyethyleneglycol, mannans, sulfated polysaccharides, mucopolysaccharides, glycoproteins, and β-glucans may be used.

Among these, mixed gels like carrageenan, locust bean, and xanthan gums, and agar are preferred to ensure gelatinization of the propolis food products.

Also, sulfated polysaccharides are preferably used as a gelatinizer since they are capable not only of gelatinizing the propolis extracts but also of thickening the product. Further, strong odor of the propolis extracts, which is caused by their resin components, is substantially eliminated through the use of sulfated polysaccharides. Acridity and pungency, which are irritating to mucous membranes, can also be reduced by using sulfated polysaccharides. Sulfated polysaccharides include chondroitin sulfate and heparin.

In view of providing the propolis food products with the ability to stimulate the immune system, β-glucans are preferably used as a gelatinizer. Preferred β-glucans include β-1,3-glucans such as curdlan, extracts of shitake mushrooms or of agarics mushrooms.

Certain kinds of herbs and fungi(mushrooms) may be added to the propolis food product to enhance the immunostimulating effect provided by β-glucans. Among such herbs are Ginko leaves, Echinacea, *Catharanthus roseus, Podophyllum peltatum L., Colchicum autumnale L.* (Saffron), *Viscum album* (Mistletoe), *Prunus armeniaca* (Apricot), β-vulgaris, Calendula, Dandelion, Chamomile, and leaves of *Eribotrya japonica,* while the effective fungi include *Ganoderma lucidium* (Reishi), *Lentinula edodes* (Shitake), *Grifola frondosa* (Maitake), Agarics, *Cordyceps militalis, Flammulina velutipes* (Enoki), and *Coriolus versicolor* (Kawaratake).

The ratio of propolis extracts in the propolis food product is preferably 2 to 25 w/w % to maximize the pharmaceutical effect of the flavonoids. When alcohol-extracted, however, the preferred amount of propolis extracts in the food product is 5 to 10 w/w %.

The amount of gelatinizer in the food product is preferably 0.01 to 10 w/w % to completely gelatinize the propolis extracts. Preferred amounts for different gelatinizing agents, carageenan, locust bean gum, xanthan gum, and agar, are 0.2 to 1.2 w/w %, 0.1 to 0.5 w/w %, 0.1 to 0.5 w/w %, and 0.1 to 0.5 w/w %, respectively.

In addition to gelatinizer(s), the propolis food product may contain such functional agents as stabilizers, surfactants, solubilizers, buffers, sweetners, condiments, suspending agents, coating agents, flavoring agents, flavors, coloring agents, pH conditioners, thickners, dispersers, preservatives, or solvents.

Exemplary stabilizers include sodium arginate, various gums or glycerol. Exemplary surfactants include sodium lauryl sulfate, or polysolbate 80. Exemplary solubilizers include ethanol. Exemplary buffers include phosphates, or carbonates. Exemplary sweetners include purified white sugar, aspertame, fruit sugar, sorbitol, xylitol, glucose, mannitol, maltose, trehalose, or palatinose. Exemplary condiments include menthol, fruit juice, or caramel.

Exemplary suspending agents include sodium arginate, gum arabic, or lactose. Exemplary coating agents include ceramics, hydroxypropylmethyl cellulose phthalate. Exemplary flavors and flavoring agents include fruits flavor, prune, or mintoil. Exemplary coloring agents include orange essence, food colors, or caramel.

Exemplary pH conditioners include citric acid, citrates, tartaric acid, tartrates, succinic acid, lactose, calsium lactose, and phosphates. Exemplary thickners include dextrin, xanthan gum, soybean lecithin, and polyethylene glycol. Exemplary dispersers include gum arabic, starches, crystallized cellulose, and lactose. Exemplary preservatives include solbic acid, solbates, benzoic acid, benzoates, and p-oxybenzoates. Exemplary solubilizers include purified water, and ethanol.

Production methods of the propolis food product will now be described. First, gelatinizing agents are added to water in an amount such that the amount of the agents in the food product will be 0.01 to 10 w/w %. This is followed by heating the solution until the agents have dissolved completely. The solution is further heated and propolis extracts are added, bit by bit, so that the amount of the extracts in the food product is 2 to 25 w/w %. The solution is completely homogenized. Sweetners and other additives necessary to form a gel are then added, and the solution is mixed until uniform.

Finally, the resulting gel-like composition is poured in a proper container such as an aluminum tube or a cup. The propolis food product is obtained after cooling the containers filled with the composition at room temperature, or at any cooling temperatures, for 30 minutes to 5 hours.

According to the embodiments of the present invention, as described above, following advantages are obtained.

According to the propolis food product of the present invention, the propolis extracts are formed into a gel. This prevents the extracts from immediately passing through the GI tract, allowing active ingredients like flavonoids in the extracts to stay in the GI tract for a prolonged period of time. Additionally, the gel has a network-like structure, which allows gradual release of flavonoids into the GI tract and prolonged contact with digestive fluids like bile acid. Consequently, the rate of absorption of the active ingredients such as flavonoids in the GI tract is significantly increased.

Also, the propolis food product according to the present invention keeps propolis extracts from contacting the mucous membranes of the gastrointestinal tract, which reduces irritation resulting from the acridity and pungency of propolis. Unpleasant odors of propolis are also reduced in the food product. As a result, the propolis food product according to the present invention can be readily ingested without water.

According to the propolis food product of the present invention, use of sulfated polysaccharides as a gelatinizer enhances the ingestability described above. Sulfated polysaccharides also help to form a gel and to thicken the product.

According to the propolis food product of the present invenion, use of β-glucans as a gelatinizer provides the food product with the ability to stimulate immune system of a human body, thereby, for example, suppressing tumors.

According to the propolis food product of the invention, propolis extracts are extracted with alcohol. This increases the extraction efficiency of the active ingredients of the propolis, such as flavonoids, and reduces the chances of contamination by microorganisms.

According to the propolis food product of the invention, the food product contains 2 to 25 w/w % propolis extracts. The food product preferably contains 5 to 10 w/w % propolis extracts when the extracts are alcohol-extracted. This maximizes the pharmaceutical effects of the flavonoids.

EXAMPLES

The embodiments of the present invention will now be described in further detail with reference to examples as well as comparative examples presented below.

Example 1

In this example, carrageenan, locust bean gum, and agar were used as gelatinizing agents.

First, 1.5 g of locust bean gum was suspended into a proper amount of water, and 5.0 g of carrageenan was added. The suspension was heated to 80 degrees Celsius to dissolve the agents. 2.5 g of agar was added to hot water in a container, which was then placed in a heat bath to dissolve the agar. While stirring, the agar solution was added to the locust bean/carrageenan solution.

Next, 0.6 g of potassium sorbate, 1.0 g of potassium chloride, 1.0 g of calcium lactate, and 1.2 g of aspartame were each added to the solution. While the mixture was being stirred, 66.7 g of propolis extracts was added, little by little, to form 1,000 g of uniform gel composition. The total amount of water in the composition was 920.5 g. The gel composition was then poured into aluminum stick-type containers or cups, each having the same volume. The containers were then sealed and cooled, at room temperature or in an ice bath, to form the propolis food product.

Example 2

In this example, carrageenan, locust bean gum, xanthan gum, agar, and chondroitin sulfate were used as gelatinizers.

First, 2.5 g of locust bean gum was suspended into a proper amount of water, and 2.5 g of carrageenan as well as 1.0 g of chondroitin sulfate was added. The suspension was heated to 80 degrees Celsius to dissolve the agents. 3.5 g of agar and 1.5 g of xanthan gum were added to hot water in a container, which was placed in a heat bath to dissolve the agents. This solution was added to the solution containing carrageenan, locust bean and chondroitin sulfate while stirring.

Next, 0.6 g of potassium sorbate and 1.2 g of aspartame were each added to the solution. While the mixture was being stirred, 66.7 g of propolis extracts were added, little by little, to the solution to form 1,000 g of uniform gel composition. The total amount of water in the composition was 920.5 g. The gel composition was then poured into aluminum stick-type containers, or cups, each of which had the same volume. The containers were then sealed and cooled, at room temperature or in an ice bath, to form the propolis food product.

Example 3

In this example, carrageenan and locust bean gum were used as gelatinizers, and shitake extracts and curdlan as β-glucans.

First, 2.0 g of locust bean gum was suspended into a proper amount of water, and 5.0 g of carrageenan and 2.0 g of shitake extracts were added. The solution was heated to 80 degrees Celsius to dissolve the agents. A 1 w/w % curdlan suspension was prepared by dissolving 1.0 g of curdlan into water. The suspension was homogenized using a mixer. The locust bean gum/carrageenan/shitake extracts solution was added to this solution while the mixture was being stirred.

Next, 0.6 g of potassium sorbate, 1.0 g of calcium lactate, and 1.2 g of aspartame were each added to the solution. While the mixture was well stirred, 66.7 g of propolis extracts was added, little by little, to the solution to form 1,000 g of uniform gel composition. The amount of water in the composition was 920.5 g. The gel composition was then poured into aluminum stick-type containers or cups, each of which had the same volume. The containers were then sealed and cooled, at room temperature or in an ice tab, to form the propolis food product.

Comparative Example 1 (control 1)

In this control example, propolis extracts were used without being formed into a gel.
Flavonoids Seeping-out Rate Test Rates that Flavonoids seeped out from two samples, sample 1 and sample 2, of the propolis food product obtained in example 1 were measured. Measurements were taken at 0, 10, 20, 30, 45, 60, and at 90 minutes.

Preparation of sample solutions 5 ml portions of samples 1 and 2 were centrifuged for 10 minutes at 12,000 rpm, and each of the resulting precipitations was resuspended in 1 ml of water. The suspensions were centrifuged for another 10 minutes at 12,000 rpm. 2.5 ml of 99.5 v/v % ethanol was then added to each precipitation, and the resulting solutions were designated as sample solutions 1 and 2, respectively. Preparation of standard solutions and estimation of a calibration curve Standard solutions having quercetin concentrations of 1 mg/ml, 0.1 mg/ml, and 0.01 mg/ml, were prepared by performing a serial dilution. 50 mg of quercetin was first dissolved into 99.5 v/v % ethanol to give a 50ml standard solution 1 with a quercetin concentration of 1 mg/ml, a 1 ml portion of which was then diluted by a factor of 10 with 99.5 v/v % ethanol to give a 10 ml standard solution 2 having 0.1 mg/ml quercetin concentration. A 1 ml portion of the standard solution 2 was further diluted with 99.5 v/v % ethanol by a factor of 10 to give a 10 ml standard solution 3 having a quercetin concentration of 0.01 mg/ml.

4.3 ml of 80 v/v % ethanol, 0.1 ml of 10 v/v % aluminum nitrate, and 0.1 ml of 1M potassium acetate were added to each of three 0.5 ml aliquots, which were taken from the standard solutions 1 to 3, respectively. The aliquots were allowed to stand for 40 minutes, and the absorbance of each aliquot was measured at 415 nm. A correction was made to the absorbance by subtracting the absorbance of a blank solution from that of each solution, and a calibration curve was estimated based on the corrected absorbance and the concentrations of the standard solutions 1 to 3.
Measurements of Absorbance 4.3 ml of 80 v/v % ethanol, 0.1 ml of 10 v/v % aluminum nitrate, and 0.1 ml of 1M potassium acetate were added to each of two 0.5 ml aliquots taken from the test solutions 1 and 2, respectively. The aliquots were allowed to stand for 40 minutes, and absorbance was measured for each aliquot at 415 nm. The concentrations of flavonoids were determined based on the calibration curve, and averages were taken.

Flavonoid concentrations of the sample solutions 1 and 2 were measured at 0, 10, 20, 30, 45, 60, and 90 minutes, and the seep-out rate of flavonoids was calculated as the ratio of the flavonoid concentration at each time interval to the flavonoid concentration at time 0. The same procedures were followed with the propolis extracts of control 1. The results are shown in Table 1 and in FIG. 1. In FIG. 1, the horizontal axis corresponds to time in minutes and the vertical axis to the seep-out rate in percent.

TABLE 1

| time (min) | Example 1 seep-out ratio (%) | Control 1 seep-out ratio (%) |
| --- | --- | --- |
| 0 | 0.0 | 0.0 |
| 10 | 13.5 | 98.4 |
| 20 | 34.1 | 101.3 |
| 30 | 54.3 | 102.0 |
| 45 | 78.1 | 101.2 |
| 60 | 92.3 | 100.1 |
| 90 | 103.6 | 99.8 |

As can be seen in Table 1 and FIG. 1, flavonoids seeped out from the propolis food product of example 1 significantly more slowly when compared to the food product of control 1. This indicates that by forming propolis extracts into a gel, one can improve the bio-absorption efficiency of flavonoids, since flavonoids in the propolis food product so produced remain in the GI tract for a longer time. Evaluation of mucous membrane irritancy of the propolis food product.

The degree of irritation to humans was evaluated by giving the food products to 20 subjects, both men and women, whose ages ranged from the 20's to the 70's. The subjects were given the gelatinized propolis food products of examples 1 to 3, and propolis extracts of control 1. The extracts of control 1 were added to water, without being formed into a gel, in an amount so that the extract content would be 6.67 w/w %.

The food products and propolis extracts were evaluated for three gastatory properties, namely, acridity, pungency, and palatability. Each property was graded as follows. For acridity, 3 points were assigned to each food product that was not deemed acrid by a subject. One point was assigned to each food product that was considered a little acrid by a subject, and no points were assigned to each food product that was considered acrid by a subject. For pungency, 3 points were assigned to each food product that was not considered pungent. One point was assigned to each food product that was considered a little pungent by a subject, and no points were assigned to each food product that was considered pungent. For palatability, 3 points were assigned to each food product that was considered good by a subject. One point was assigned to each food product that was considered acceptable, and no points were given to a food product that was deemed unpalatable by a subject. The results are shown in Table 2.

TABLE 2

|  | Example 1 | Example 2 | Example 3 | Control 1 |
|---|---|---|---|---|
| acridity | 46 pts | 52 pts | 48 pts | 6 pts |
| pungency | 32 pts | 42 pts | 45 pts | 5 pts |
| palatability | 46 pts | 42 pts | 48 pts | 8 pts |

As shown in Table 2, acridity and pungency were reduced while palatability was improved in the propolis food product of examples 1 to 3, when compared to those of control 1.

Example 4

In this example, a propolis food product was prepared using agar as a gelatinizer.

The propolis food product was prepared by dispersing 5 ml of propolis extracts along with 0.7 g of agar in 20 ml distilled water.

Example 5

In this example, propolis food product was prepared using β-glucans as a gelatinizing agent.

The propolis food product was prepared by dispersing 5 ml of propolis extracts, along with 0.52 g of shitake extracts and curdlan as β-glucans, in 20 ml distilled water.

Evaluation of the Immuno-Stimulating Activity

The propolis food products of examples 4 and 5 were evaluated for tumor-suppressing effects, which are indicative of ability of the food product to stimulate immune system of a living organism.

Figure 2:
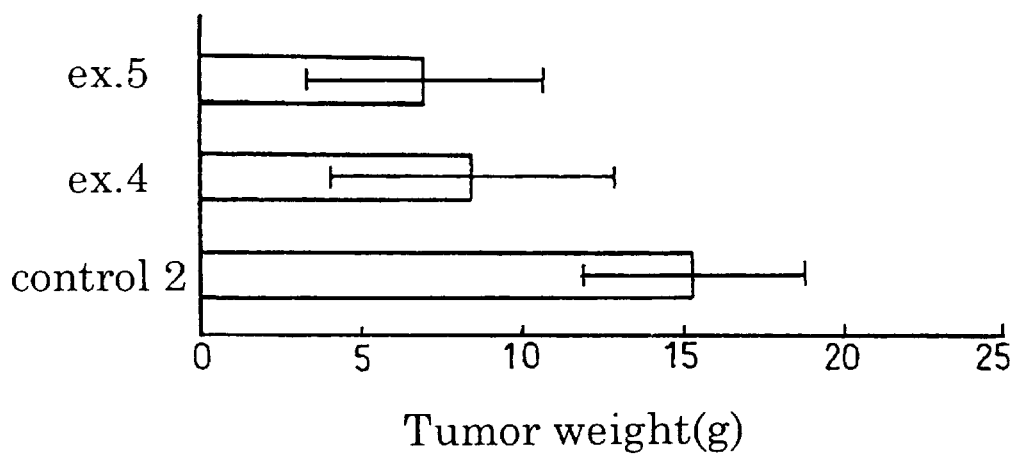
FIG. 2 is a graph showing tumor weight for each sample.

Sarcoma-180 tumor cells were placed subcutaneously in mice ($10^5$ cells per/mouse). Beginning 4 days prior to the implantation of the cells, the propolis food products of examples 4 and 5 were orally and forcibly administered to mice. The mice were fed 1.7 g per 1 kg of animal weight per day. Tumor weights were measured 25 days after the cell implantation. In contrast, no propolis food products were given to control mice, which had the tumor cells similarly implanted. Tumors were collected 25 days after the implantation and weights were measured. The results are shown in Table 3 and FIG. 2. In FIG. 2, the horizontal axis corresponds to the weights of tumor in grams, with each bar corresponding to a different group. The horizontal lines lying across the tip of each bar represent the standard deviation (σ) for each group.

TABLE 3

|  | Example 4 | Example 5 | Control 2 |
|---|---|---|---|
| weight (g) ± SD (σ) | 8.466 ± 4.162 | 6.987 ± 4.062 | 15.308 ± 4.086 |

As shown in Table 3 and FIG. 2, tumor growths were significantly suppressed in the mice given the propolis food of examples 4 and 5, whereas no growth suppression was observed in the control group. Weights of the tumors collected from the mice that were fed with the propolis food products of examples 4 and 5 were smaller than that of the control group by as much as 44.8 % and 54.4 %, respectively. The tumor suppressing effect of the propolis food product of example 5, which used β-glucans as a gelatinizing agent, was greater than that of example 4 by 17.3 %. Accordingly, the propolis food products proved to have the ability to stimulate the immune system of a living organism. This ability is even enhanced if β-glucans are used as a gelatinizing agent.

Alternative embodiments of the present invention as presented below are also possible.

The propolis food products of the present invention may be gelatinized by placing propolis extracts in a moist environment or by heating them. The bio-absorbability of propolis extracts in such food product is increased.

The propolis food products of the present invention may contain sulfated saccharides and β-glucans as gelatinizers. The propolis food products so composed have enhanced immuno-stimulating activity and are capable of protecting mucous membranes.

The propolis food products of the present invention may contain from 2 to 25 w/w % of the propolis extracts. This assures the pharmaceutical effects of propolis extracts.

The gelatinizers preferably make up from 0.01 to 10 w/w % of the food product. Thus, the food product is gelatinized with small amount of the gelatinizers.

The propolis food products of the present invention may be produced by first adding the gelatinizers to water in an amount so that the gelatinizers contained in the propolis food product are from 0.01 to 10 w/w %, then dissolving the gelatinizers to form a uniform solution, then adding the propolis extracts to the solution so that the propolis extracts contained in the food products are from 2 to 25 w/w %, and then homogenizing the propolis extracts in the solution.

The propolis food products of the present invention may contain two or more gelatinizers. This ensures the gelatinization of the propolis extracts.

It should be apparent to those skilled in the art that the present invention may be embodied in many other specific forms without departing from the spirit or scope of the invention. Therefore, the present examples and embodiments are to be considered as illustrative and not restrictive, and the invention is not to be limited to the details given herein, but may be modified within the scope and equivalence of the appended claims.

What is claimed is:

1. A propolis food product having a gelatinous form comprising:

propolis extracts being extracted by alcohol extraction, wherein the content of the propolis extracts in the food product is between 5 and 10 wt. %; and a gelatinizer for gelatinizing the propolis extracts, wherein the gelatinizer comprises at least one selected from the group consisting of sulfated saccharides, curdlan, agarics extracts, shiitake extracts, carrageenan, locust bean gum, xanthan gum, and agar.

2. The propolis food product according to claim 1 wherein the sulfated polysaccharides comprise chondroitin sulfate, heparin, or a combination thereof.

3. The propolis food product according to claim 1, comprising at least one herb selected from the group consisting of Ginko leaves, Echinacea, *Catharanthus roseus*, *Podophyllum peltatum L.*, *Colchicum autumnale L.* (Saffron), *Viscum album* (Mistletoe), *Prunus armeniaca* (Apricot), β-vulgaris, Calendula, Dandelion, Chamomile, and leaves of *Eribotrya japonica*.

4. The propolis food product according to claim 1, comprising at least one fungus selected from the group consisting of *Ganoderma lucidium* (Reishi), *Lentinula edodes* (Shitake), *Grifola frondosa* (Maitake), Agarics, *Cordyceps militalis*, *Flammulina velutipes* (Enoki), and *Coriolus versicolor* (Kawaratake).

5. The propolis food product according to claim 1, containing from 0.2 to 1.2 w/w % of carageenan.

6. The propolis food product according to claim 1, containing from 0.1 to 0.5 w/w % of locust bean gum.

7. The propolis food product according to claim 1, containing from 0.1 to 0.5 w/w % of xanthum gum.

8. The propolis food product according to claim 1, containing from 0.1 to 0.5 w/w % of agar.

9. A propolis food product comprising:

propolis extracts being extracted by water extraction, wherein the content of the propolis extracts is between 2 and 25 w/w % in the propolis food; and a gelatinizer for gelatinizing the propolis extracts, wherein the gelatinizer comprises at least one selected from the group consisting of sulfated saccharides, curdlan, agarics extracts, shiitake extracts, carrageenan, locust bean gum, xanthan gum, and agar.

10. A method for producing a propolis food product containing active ingredients with an improved bio-absorbability comprising the steps of:

preparing a gelatinizer solution by adding at least one gelatinizer to water so that the amount of the gelatinizer in the food product is from 0.01 to 10 w/w %;

extracting a propolis extract using water extraction;

adding the propolis extracts to the gelatinizer solution so that the amount of the propolis extracts in the food product is from 2 to 25 w/w %; and forming a gel composition by admixing the solution to disperse the propolis extracts uniformly throughout the solution.

11. A method for producing a propolis food product containing active ingredients with an improved bio-absorbability comprising the steps of:

preparing a gelatinizer solution by adding at least one gelatinizer to water so that the amount of the gelatinizer in the food product is from 0.01 to 10 w/w %;

extracting a propolis extract using alcohol extraction;

adding the propolis extracts to the gelatinizer solution so that the amount of the propolis extracts in the food product is from 5 to 10 w/w %; and forming a gel composition by admixing the solution to disperse the propolis extracts uniformly throughout the solution.

12. A propolis food product prepared from a mixture comprising:

about 5 ml of propolis extracts;

about 0.7 g of agar as a gelatinizer; and about 20 ml of diluted water.

13. A propolis food product prepared from a mixture comprising:

about 5 ml of propolis extracts;

about 0.52 g of shiitake extracts as a gelatinizer and containing a β-glucan; and about 20 ml of diluted water.

* * * * *